(12) United States Patent
Kyushima et al.

(10) Patent No.: US 8,477,907 B2
(45) Date of Patent: *Jul. 2, 2013

(54) SOLID-STATE IMAGE PICKUP APPARATUS AND X-RAY INSPECTION SYSTEM

(75) Inventors: Ryuji Kyushima, Hamamatsu (JP); Kazuki Fujita, Hamamatsu (JP); Harumichi Mori, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/989,132

(22) PCT Filed: Apr. 22, 2009

(86) PCT No.: PCT/JP2009/058003
§ 371 (c)(1),
(2), (4) Date: Dec. 2, 2010

(87) PCT Pub. No.: WO2009/131150
PCT Pub. Date: Oct. 29, 2009

(65) Prior Publication Data
US 2011/0064195 A1    Mar. 17, 2011

(30) Foreign Application Priority Data
Apr. 24, 2008    (JP) .............................. P2008-114210

(51) Int. Cl.
    *H05G 1/64*    (2006.01)
(52) U.S. Cl.
    USPC ............................ 378/98.8; 378/114; 378/115
(58) Field of Classification Search
    USPC ............. 378/98.8, 114, 115, 116; 250/370.09
    See application file for complete search history.

(56) References Cited

U.S. PATENT DOCUMENTS

| | | | |
|---|---|---|---|
| 2004/0202281 A1 | 10/2004 | Colbeth et al. | |
| 2009/0218476 A1* | 9/2009 | Kameshima et al. | 250/208.1 |
| 2011/0299654 A1* | 12/2011 | Mori et al. | 378/62 |

FOREIGN PATENT DOCUMENTS

| | | |
|---|---|---|
| JP | 63-185284 | 7/1988 |
| JP | 2005-184358 | 7/2005 |

(Continued)

OTHER PUBLICATIONS

Translation of JP 2005-184358 published on Jul. 7, 2005.*

*Primary Examiner* — Glen Kao
(74) *Attorney, Agent, or Firm* — Drinker Biddle & Reath LLP

(57) ABSTRACT

A solid-state image pickup apparatus 1A includes a photodetecting section 10A, a signal readout section 20, and a controlling section 40A. In the photodetecting section 10A, M×N pixel units $P_{1,1}$ to $P_{M,N}$ each including a photodiode and a readout switch are arrayed in M rows and N columns. Charges generated in each pixel unit $P_{m,n}$ are input to an integrating circuit $S_n$ through a readout wiring $L_{O,n}$, and a voltage value output from the integrating circuit $S_n$ in response to the charge amount is output through a holding circuits $H_n$. When in a first imaging mode, a voltage value according to an amount of charges generated in the photodiode PD of each of the M×N pixel units $P_{1,1}$ to $P_{M,N}$ in the photodetecting section 10A is output from the signal readout section 20. When in a second imaging mode, a voltage value according to an amount of charges generated in the photodiode PD of each pixel unit $P_{m,n}$ included in consecutive $M_1$ rows in the photodetecting section 10A is output from the signal readout section 20.

10 Claims, 9 Drawing Sheets

FOREIGN PATENT DOCUMENTS

| | | |
|---|---|---|
| JP | 2006-068512 | 3/2006 |
| JP | 2007-050053 | 3/2007 |
| JP | 2007-144064 | 6/2007 |
| JP | 2007-289281 | 11/2007 |
| WO | 2006/109808 | 10/2006 |
| WO | WO 2007/046372 | 4/2007 |

\* cited by examiner

SOLID-STATE IMAGE PICKUP APPARATUS AND X-RAY INSPECTION SYSTEM

TECHNICAL FIELD

The present invention relates to a solid-state image pickup apparatus and an X-ray inspection system.

BACKGROUND ART

Solid-state image pickup apparatuses using the CMOS technique are known, and among these, a passive pixel sensor (PPS) type solid-state image pickup apparatus is known. The PPS type solid-state image pickup apparatus includes a photodetecting section where PPS type pixel units including photodiodes for generating charges of amounts according to incident light intensities are two-dimensionally arrayed in M rows and N columns, accumulates, in a capacitor of an integrating circuit, charges generated in the photodiode in response to light incidence in each pixel unit, and outputs a voltage value according to the accumulated charge amount.

Generally, an output terminal of each of the M pixel units of each column is connected with an input terminal of an integrating circuit provided corresponding to the column via a readout wiring provided corresponding to the column. And, in sequence from the first row to the M-th row and row by row, charges generated in the photodiodes of the pixel units are input to a corresponding integrating circuit through a corresponding readout wiring, and a voltage value according to the charge amount is output from the integrating circuit.

The PPS type solid-state image pickup apparatus is used for various purposes, and used, for example, in combination with a scintillator section as an X-ray flat panel also for medical purposes and industrial purposes, and further specifically used also in an X-ray CT apparatus, a microfocus X-ray inspection system, etc. An X-ray inspection system disclosed in Patent Document 1 is a system that images X-rays output from an X-ray generator and transmitted through an inspection object by a solid-state image pickup apparatus to inspect the inspection object, and is capable of imaging X-rays transmitted through the inspection object by the solid-state image pickup apparatus in a plurality of types of imaging modes. These multiple types of imaging modes are mutually different in an imaging region in the photodetecting section.

CITATION LIST

Patent Literature

Patent Document 1: Pamphlet of International Publication No. WO2006/109808

SUMMARY OF INVENTION

Technical Problem

In Patent Document 1, there is a description to the effect of differentiating the imaging region in the photodetecting section of the solid-state image pickup apparatus depending on the imaging mode, but there is no disclosure of the configuration and operation of the solid-state image pickup apparatus. However, the inventor of the present invention has discovered that a problem exists such that the solid-state image pickup apparatus cannot perform a high-speed operation depending on the configuration of the solid-state image pickup apparatus.

The present invention has been made in order to solve the above problem, and an object thereof is to provide a solid-state image pickup apparatus and an X-ray inspection system that can perform a high-speed operation.

Solution to Problem

A solid-state image pickup apparatus according to the present invention includes (1) a photodetecting section having M×N pixel units $P_{1,1}$ to $P_{M,N}$ two-dimensionally arranged in M rows and N columns, each of the pixel units including a photodiode and a readout switch connected with the photodiode, the photodiode generating charges corresponding to an intensity of an incident light, (2) a readout wiring $L_{O,n}$ connected with a readout switch of each of the M pixel units $P_{1,n}$ to $P_{M,n}$ of an n-th column in the photodetecting section, for reading out charges generated in the photodiode of any pixel unit of the M pixel units $P_{1,n}$ to $P_{M,n}$ via the readout switch of the pixel unit, (3) a signal readout section connected with each of the readout wirings $L_{O,1}$ to $L_{O,N}$, for holding a voltage value according to an amount of charges input through the readout wiring $L_{O,n}$, and sequentially outputting the held voltage values, and (4) a controlling section that controls an opening and closing operation of the readout switch of each of the M×N pixel units $P_{1,1}$ to $P_{M,N}$ in the photodetecting section and controls an output operation of a voltage value in the signal readout section to make a voltage value according to an amount of charges generated in the photodiode of each of the M×N pixel units $P_{1,1}$ to $P_{M,N}$ in the photodetecting section be output from the signal readout section. Further, the controlling section, (a) when in a first imaging mode, makes a voltage value according to an amount of charges generated in the photodiode of each of the M×N pixel units $P_{1,1}$ to $P_{M,N}$ in the photodetecting section be output from the signal readout section, and (b) when in a second imaging mode, makes a voltage value according to an amount of charges generated in the photodiode of each pixel unit $P_{m,n}$ included in a specific range of consecutive $M_1$ rows in the photodetecting section be output from the signal readout section. However, M and N are each an integer not less than 2, $M_1$ is an integer less than M, m is an integer not less than 1 and not more than M, and n is an integer not less than 1 and not more than N.

In the solid-state image pickup apparatus according to the present invention, under control by the controlling section, charges generated in each pixel unit $P_{m,n}$ in response to light incidence into the photodiode are, when a readout switch of the pixel unit is closed, input to the signal readout section through the readout switch and the readout wiring $L_{O,n}$. In the signal readout section, a voltage value according to the input charge amount is output. This solid-state image pickup apparatus has a first imaging mode and a second imaging mode. Under control by the controlling section, when in the first imaging mode, a voltage value according to the amount of charges generated in the photodiode of each of the M×N pixel units $P_{1,1}$ to $P_{M,N}$ in the photodetecting section is output from the signal readout section. On the other hand, when in the second imaging mode, a voltage value according to the amount of charges generated in the photodiode of each pixel unit $P_{m,n}$ included in a specific range of consecutive $M_1$ rows in the photodetecting section is output from the signal readout section.

In the solid-state image pickup apparatus according to the present invention, the controlling section, when in the second imaging mode, preferably has as the specific range, a range of $M_1$ rows counted in order from the row closest to the signal readout section out of the M rows in the photo detecting section, and makes a voltage value according to the amount of charges generated in the photodiode of each pixel unit $P_{m,n}$ in the specific range be output from the signal readout section.

The solid-state image pickup apparatus according to the present invention preferably further includes, between the specific range in the photodetecting section and another range excluding the specific range, a disconnecting switch provided on each readout wiring $L_{O,n}$, and the controlling section preferably closes the disconnecting switch when in the first imaging mode, and opens the disconnecting switch when in the second imaging mode.

The solid-state image pickup apparatus according to the present invention preferably includes discharging means that discharges a junction capacitance section of the photodiode in each pixel unit $P_{m,n}$ of another range excluding the specific range in the photodetecting section when in the second imaging mode.

In the solid-state image pickup apparatus according to the present invention, the controlling section preferably differentiates a gain being a ratio of an output voltage value to an input charge amount in the signal readout section between the first imaging mode and second imaging mode.

The solid-state image pickup apparatus according to the present invention preferably further includes a scintillator section that is provided so as to cover the M×N pixel units $P_{1,1}$ to $P_{M,N}$ in the photodetecting section.

Moreover, an X-ray inspection system according to the present invention includes the solid-state image pickup apparatus according to the present invention described above and an X-ray generator, and images X-rays output from the X-ray generator and transmitted through an inspection object by the solid-state image pickup apparatus to inspect the inspection object. Moreover, it is preferable that the X-ray generator outputs X-rays at a predetermined divergence angle when in a first output mode, and outputs X-rays at a narrower divergence angle than the predetermined divergence angle when in a second output mode, and that the solid-state image pickup apparatus operates in the first imaging mode when the X-ray generator outputs X-rays in the first output mode, and the solid-state image pickup apparatus operates in the second imaging mode when the X-ray generator outputs X-rays in the second output mode.

Advantageous Effects of invention

The solid-state image pickup apparatus according to the present invention can perform a high-speed operation.

DESCRIPTION OF EMBODIMENTS

Figure 1:
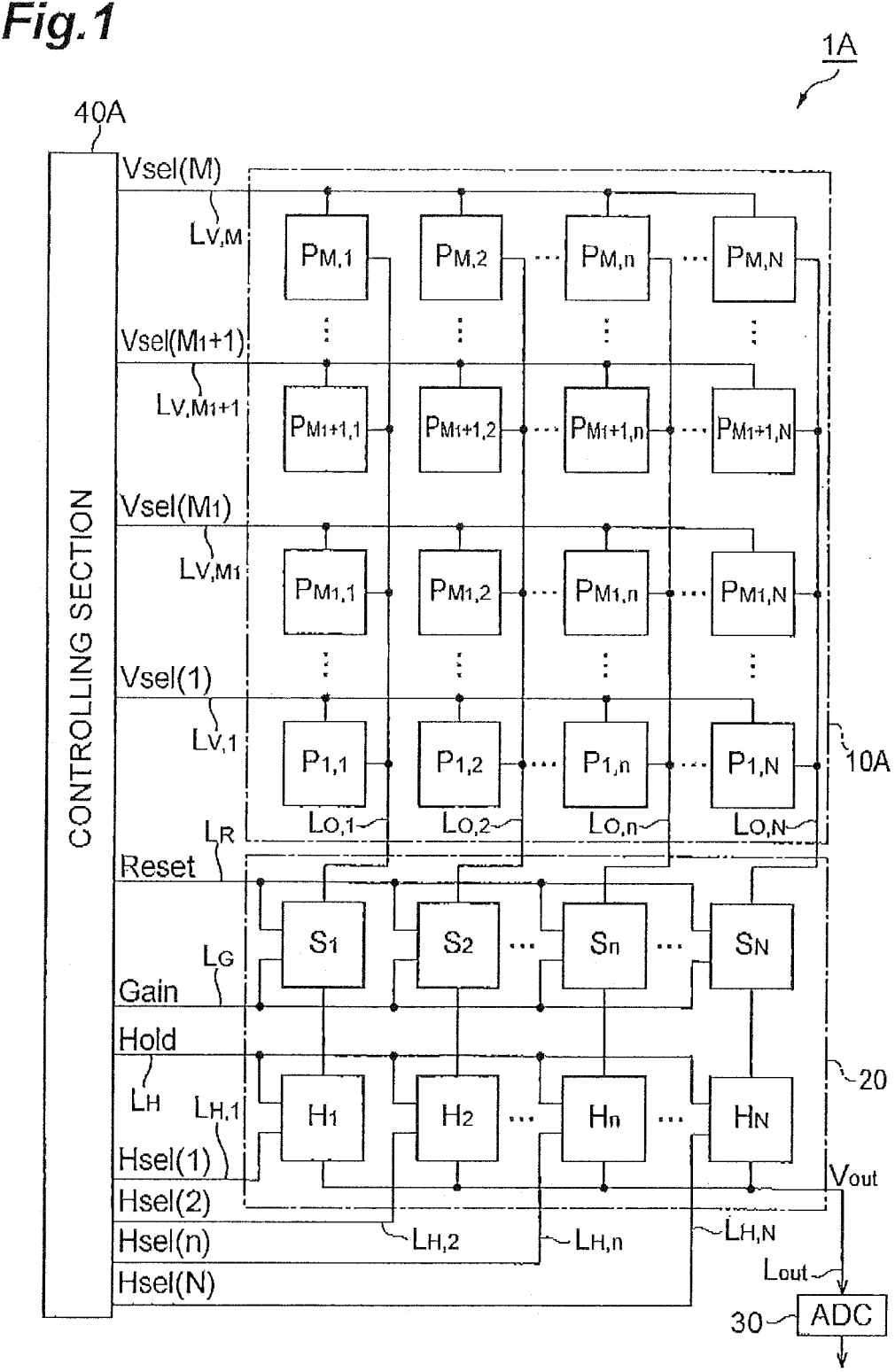
FIG. 1 is a view showing a configuration of a solid-state image pickup apparatus 1A according to a first embodiment.

Hereinafter, a best mode for carrying out the present invention will be described in detail with reference to the accompanying drawings. Also, the same components will be denoted with the same reference numerals in the description of the drawings, and overlapping description will be omitted.

First, description will be given of a solid-state image pickup apparatus 1A according to a first embodiment. FIG. 1 is a view showing a configuration of the solid-state image pickup apparatus 1A according to the first embodiment. The solid-state image pickup apparatus 1A shown in this figure includes a photodetecting section 10A, a signal readout section 20, an A/D converting section 30, and a controlling section 40A. Moreover, in the case of use as one for X-ray detection, a scintillator section is provided so as to cover the photodetecting section 10A of the solid-state image pickup apparatus 1A.

For the photodetecting section 10A, M×N pixel units $P_{1,1}$ to $P_{M,N}$ are two-dimensionally arrayed in M rows and N columns. A pixel unit $P_{m,n}$ is located on the m-th row and the n-th column. The pixel units $P_{m,n}$ are arrayed at a pitch of, for example, 100 μm. Here, M and N are each an integer not less than 2, m is an integer not less than 1 and not more than M, and n is an integer not less than 1 and not more than N. The pixel units are pixel units of the PPS type, and have a common configuration.

In addition, the photodetecting section 10A may have, around the M×N pixel units $P_{1,1}$ to $P_{M,N}$ two-dimensionally arrayed in M rows and N columns, pixel units including photodiodes. However, these surrounding pixel units, which are covered with a shielding portion that prevents incidence of X-rays into the signal readout section 20 and the like and where no light is made incident and no charge is generated, thus do not contribute to imaging. The photodetecting section 10A includes at least the M×N pixel units $P_{1,1}$ to $P_{M,N}$ two-dimensionally arrayed in M rows and N columns as effective pixel units for imaging.

Each of the N pixel units $P_{m,1}$ to $P_{m,N}$ of the m-th row is connected with the controlling section 40A by an m-th row selecting wiring $L_{V,m}$. An output terminal of each of the M pixel units $P_{1,n}$ to $P_{M,n}$ of the n-th column is connected with an integrating circuit $S_n$ of the signal readout section 20 by an n-th column readout wiring $L_{O,n}$.

The signal readout section 20 includes N integrating circuits $S_1$ to $S_N$ and N holding circuits $H_1$ to $H_N$. The integrating circuits $S_n$ have a common configuration. Moreover, the holding circuits have a common configuration.

Each integrating circuit $S_n$ has an input terminal connected with the readout wiring $L_{O,n}$, accumulates charges input to this input terminal, and outputs a voltage value according to the accumulated charge amount from an output terminal to the holding circuit $H_n$. Each of the N integrating circuits $S_1$ to $S_N$ is connected with the controlling section 40A by a reset wiring $L_R$, and also connected with the controlling section 40A by a gain setting wiring $L_G$.

Each holding circuit $H_n$ has an input terminal connected with the output terminal of the integrating circuit $S_n$, holds a voltage value input to this input terminal, and outputs the held voltage value from an output terminal to a voltage outputting wiring $L_{out}$. Each of the N holding circuits $H_1$ to $H_N$ is connected with the controlling section 40A by a holding wiring $L_H$. Moreover, each holding circuit $H_n$ is connected with the controlling section 40A by an n-th column selecting wiring $L_{H,n}$.

The A/D converting section 30 is input with a voltage value output to the voltage outputting wiring $L_{out}$ from each of the N holding circuits $H_1$ to $H_N$, and applies A/D converting to the input voltage value (analog value) to output a digital value according to the input voltage value.

The controlling section 40A outputs an m-th row selection control signal Vsel(m) to the m-th row selecting wiring $L_{V,m}$ to supply this m-th row selection control signal Vsel(m) to each of the N pixel units $P_{m,1}$ to $P_{m,N}$ of the m-th row. M row selection control signals Vsel(1) to Vsel(M) sequentially take significant values. The controlling section 40A includes a shift register to sequentially output M row selection control signals Vsel(1) to Vsel(M) as significant values. The controlling section 40A includes a shift register to sequentially output M row selection control signals Vsel(1) to Vsel(N) as significant values.

The controlling section 40A outputs an n-th column selection control signal Hsel(n) to the n-th column selecting wiring $L_{H,n}$ to supply this n-th column selection control signal Hsel(n) to the holding circuit $H_n$. N column selection control signals Hsel(1) to Hsel(N) also sequentially take significant values. The controlling section 40A includes a shift register to sequentially output N column selection control signals Hsel(1) to Hsel(N) as significant values.

Moreover, the controlling section 40A outputs a reset control signal Reset to the reset wiring $L_R$ to supply this reset control signal Reset to each of the N integrating circuits $S_1$ to $S_N$. The controlling section 40A outputs a gain setting signal Gain to the gain setting wiring $L_G$ to supply this gain setting signal Gain to each of the N integrating circuits $S_1$ to $S_N$. The controlling section 40A outputs a hold control signal Hold to the holding wiring $L_H$ to supply this hold control signal Hold to each of the N holding circuits $H_1$ to $H_N$. Further, although not shown, the controlling section 40A also controls A/D converting in the A/D converting section 30.

The controlling section 40A, as in the above, controls an opening and closing operation of a readout switch $SW_1$ in each of the M×N pixel units $P_{1,1}$ to $P_{M,N}$ in the photodetecting section 10A, and controls a holding operation and an output operation of a voltage value in the signal readout section 20. Accordingly, the controlling section 40A makes a voltage value according to the amount of charges generated in the photodiode of each of the M×N pixel units $P_{1,1}$ to $P_{M,N}$ in the photodetecting section 10A be repeatedly output as frame data from the signal readout section 20.

Figure 2:
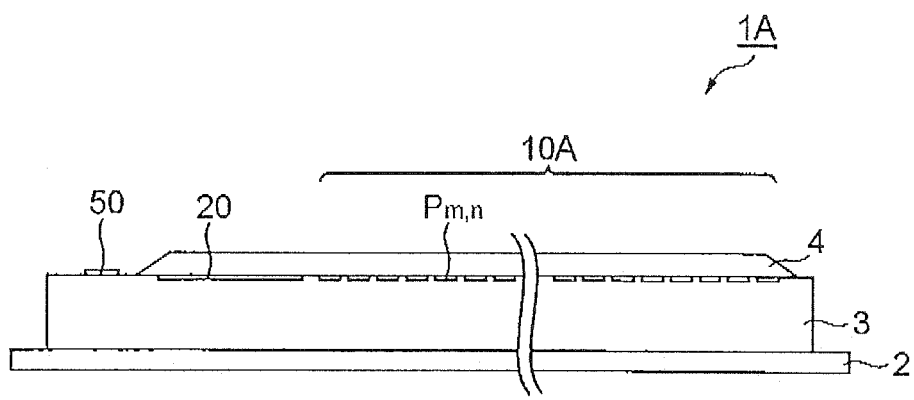
FIG. 2 is a view showing a section of the solid-state image pickup apparatus 1A according to the first embodiment.

FIG. 2 is a view showing a section of the solid-state image pickup apparatus 1A according to the first embodiment. For the solid-state image pickup apparatus 1A, a semiconductor substrate 3 is adhered to a flat plate-like base member 2, and a scintillator section 4 is provided on the semiconductor substrate 3. On a main surface of the semiconductor substrate 3, the photodetecting section 10A where the pixel units $P_{m,n}$ are arrayed, the signal readout section 20, the A/D converting section 30, and the controlling section 40A are formed and integrated, and a bonding pad 50 for signal input/output or power supply is formed. The scintillator section 4 is provided so as to cover the M×N pixel units $P_{1,1}$ to $P_{M,N}$ in the photodetecting section 10A. The scintillator section 4 may be provided by vapor deposition on the semiconductor substrate 3. In addition, each of the signal readout section 20, the A/D converting section 30, and the controlling section 40A may be integrated not on the semiconductor substrate 3 on which the photodetecting section 10A is integrated, but on a semiconductor substrate separate from the semiconductor substrate 3.

Figure 3:
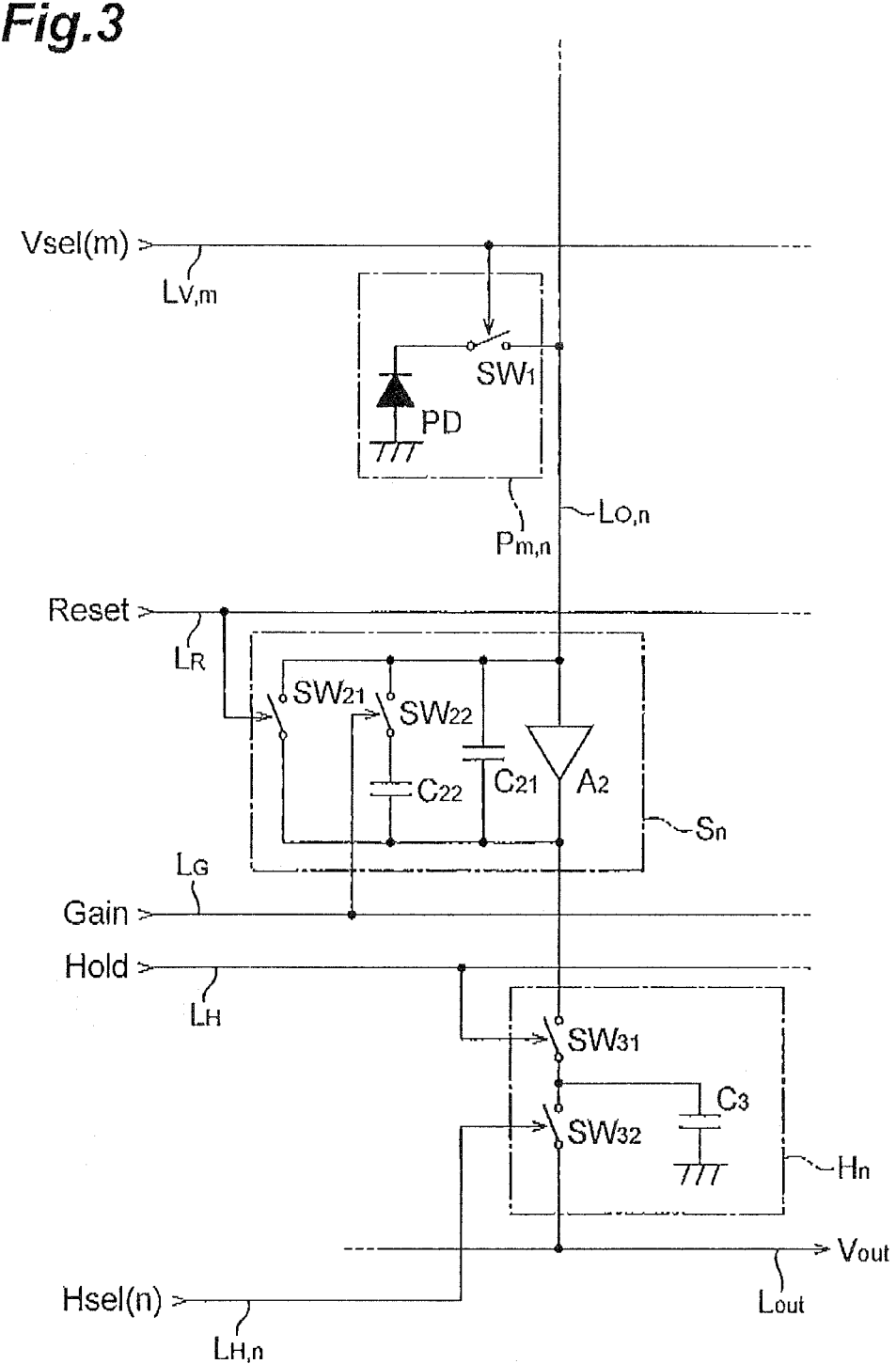
FIG. 3 is a circuit diagram of each of the pixel unit $P_{m,n}$, the integrating circuit $S_n$, and the holding circuit $H_n$ of the solid-state image pickup apparatus 1A according to the first embodiment.

FIG. 3 is a circuit diagram of each of the pixel unit including circuit $S_n$, and the holding circuit $H_n$ of the solid-state image pickup apparatus 1A according to the first embodiment. Here, a circuit diagram of the pixel unit $P_{m,n}$ as a representative of the M×N pixel units $P_{1,1}$ to $P_{M,N}$ is shown, a circuit diagram of the integrating circuit $S_n$ as a representative of the N integrating circuits $S_1$ to $S_N$ is shown, and a circuit diagram of the holding circuit $H_n$ as a representative of the N holding circuits $H_1$ to $H_N$ is shown. That is, circuit portions relating to the pixel unit $P_{m,n}$ on the m-th row and the n-th column and the n-th column readout wiring $L_{O,n}$ are shown.

The pixel unit $P_{m,n}$ includes a photodiode PD and a readout switch $SW_1$. The anode terminal of the photodiode PD is grounded, and the cathode terminal of the photodiode PD is connected with the n-th column readout wiring $L_{O,n}$ via the readout switch $SW_1$. The photodiode PD generates charges of an amount according to an incident light intensity, and accumulates the generated charges in a junction capacitance section of the photodiode PD itself. The readout switch $SW_1$ is supplied with an m-th row selection control signal Vsel(m) passed through the m-th row selecting wiring $L_{V,m}$ from the controlling section 40A. The m-th row selection control signal Vsel(m) is a signal that instructs an opening and closing operation of the readout switch $SW_1$ in each of the N pixel units $P_{m,1}$ to $P_{m,N}$ of the m-th row in the photo detecting section 10A.

In this pixel unit $P_{m,n}$, when the m-th row selection control signal Vsel(m) is at low level, the readout switch $SW_1$ opens, and charges generated in the photodiode PD are not output to the n-th column readout wiring $L_{O,n}$ but are accumulated in the junction capacitance section of the photodiode PD itself. On the other hand, when the m-th row selection control signal Vsel(m) is at high level, the readout switch $SW_1$ closes, and the charges generated in the photodiode PD and accumulated in the junction capacitance section of the photodiode PD itself until then are output to the n-th column readout wiring $L_{O,n}$ through the readout switch $SW_1$.

The n-th column readout wiring $L_{O,n}$ is connected with the readout switch $SW_1$ in each of the M pixel units $P_{1,n}$ to $P_{M,n}$ the n-th column in the photodetecting section 10A. The firth column readout wiring $L_{O,n}$ reads out charges generated in the photodiode PD included in any of the M pixel units $P_{1,n}$ to $P_{M,n}$ via the readout switch $SW_1$ in this pixel unit, and transfers the charges to the integrating circuit $S_n$.

The integrating circuit $S_n$ includes an amplifier $A_2$, an integrating capacitor $C_{21}$; an integrating capacitor $C_{22}$, a discharging switch $SW_{21}$, and a gain setting switch $SW_{22}$. The integrating capacitor $C_{21}$ and the discharging switch $SW_{21}$ are connected in parallel to each other, and provided between an input terminal and an output terminal of the amplifier $A_2$. Moreover, the integrating capacitor $C_{22}$ and the gain setting switch $SW_{22}$ are connected in series to each other, and provided between an input terminal and an output terminal of the amplifier $A_2$, so that the gain setting switch $SW_{22}$ is connected to the input terminal side of the amplifier $A_2$. The input terminal of the amplifier $A_2$ is connected with the n-th column readout wiring $L_{O,n}$.

The discharging switch $SW_{21}$ is supplied with a reset control signal Reset through the reset wiring $L_R$ from the controlling section 40A. The reset control signal Reset is a signal that instructs an opening and closing operation of the discharging switch $SW_{21}$ in each of the N integrating circuits $S_1$ to $S_N$. The gain setting switch $SW_{22}$ is supplied with a gain setting signal Gain through the gain setting wiring $L_G$ from the controlling section 40A. The gain setting signal Gain is a signal that instructs an opening and closing operation of the gain setting switch $SW_{22}$ in each of the N integrating circuits $S_1$ to $S_N$.

In this integrating circuit $S_n$, the integrating capacitors $C_{21}$, $C_{22}$ and the gain setting switch $SW_{22}$ compose a feedback capacitance section where the capacitance value is variable. That is, when the gain setting signal Gain is at low level and the gain setting switch $SW_{22}$ is open, the capacitance value of the feedback capacitance section is equal to a capacitance value of the integrating capacitor $C_{21}$. On the other hand, when the gain setting signal Gain is at high level and the gain setting switch $SW_{22}$ is open, the capacitance value of the feedback capacitance section is equal to a sum of respective capacitance values of the integrating capacitors $C_{21}$, $C_{22}$. When the reset control signal Reset is at high level, the discharging switch $SW_{21}$ closes, the feedback capacitance section is discharged, and a voltage value to be output from the integrating circuit $S_n$ is initialized. On the other hand, when the reset control signal Reset is at low level, the discharging switch $SW_{21}$ opens, charges input to the input terminal are accumulated in the feedback capacitance section, and a voltage value according to the accumulated charge amount is output from the integrating circuit $S_n$.

The holding circuit $H_n$ includes an input switch $SW_{31}$, an output switch $SW_{32}$, and a holding capacitor $C_3$. One end of the holding capacitor $C_3$ is grounded. The other end of the holding capacitor $C_3$ is connected with the output terminal of the integrating circuit $S_n$ via the input switch $SW_{31}$, and connected with the voltage outputting wiring $L_{out}$ via the output switch $SW_{32}$. The input switch $SW_{31}$ is supplied with a hold control signal Hold passed through the holding wiring $L_H$ from the controlling section 40A. The hold control signal Hold is a signal that instructs an opening and closing operation of the input switch $SW_{31}$ in each of the N holding circuits $H_1$ to $H_N$. The output switch $SW_{32}$ is supplied with an n-th column selection control signal Hsel(n) passed through the n-th column selecting wiring $L_{H,n}$ from the controlling section 40A. The n-th column selection control signal Hsel(n) is a signal that instructs an opening and closing operation of the output switch $SW_{32}$ of the holding circuit $H_n$.

In this holding circuit $H_n$, when the hold control signal Hold switches from high level to low level, the input switch $SW_{31}$ switches from a closed state to an open state, and a voltage value being input to the input terminal at this time is held in the holding capacitor $C_3$. Moreover, when the n-th column selection control signal Hsel(n) is at high level, the output switch $SW_{32}$ closes, and the voltage value held in the holding capacitor $C_3$ is output to the voltage outputting wiring $L_{out}$.

The controlling section 40A, when outputting a voltage value according to a received light intensity in each of the N pixel units $P_{m,1}$ to $P_{m,N}$ of the m-th row in the photodetecting section 10A, instructs temporary closing and then opening of the discharging switch $SW_{21}$ in each of the N integrating circuits $S_1$ to $S_N$ by a reset control signal Reset, and then instructs closing of the readout switch $SW_1$ in each of the N pixel units $P_{m,1}$ to $P_{m,N}$ of the m-th row in the photodetecting section 10A for a predetermined period by an m-th row selection control signal Vsel(m). The controlling section 40A, in this predetermined period, instructs switching of the input switch $SW_{31}$ in each of the N holding circuits $H_1$ to $H_N$ from a closed state to an open state by a hold control signal Hold. Then, the controlling section 40A, after the predetermined period, instructs sequential closing of the output switches $SW_{32}$ in the respective N holding circuits $H_1$ to $H_N$ for a predetermined period by column selection control signals Hsel(1) to Hsel(N). The controlling section 40A performs such control as in the above for the respective rows in sequence.

The solid-state image pickup apparatus 1A according to the present embodiment particularly has a first imaging mode and a second imaging mode. The first imaging mode and the second imaging mode are mutually different in an imaging region in the photodetecting section 10A. The controlling section 40A, when in the first imaging mode, makes a voltage value according to the amount of charge generated in the photodiode PD of each of the M×N pixel units $P_{1,1}$ to $P_{M,N}$ in the photodetecting section 10A be output from the signal readout section 20. Also, the controlling section 40A, when in the second imaging mode, makes a voltage value according to the amount of charge generated in the photodiode PD of each pixel unit $P_{m,n}$ included in a specific range of consecutive $M_1$ rows in the photodetecting section 10A be output from the signal readout section 20. In addition, $M_1$ is an integer less than M.

The controlling section 40A, when in the second imaging mode, preferably has a range of $M_1$ rows counted in order from the row closest to the signal readout section 20 out of the M rows in the photodetecting section 10A as the specific range, and makes a voltage value according to the amount of charges generated in the photodiode PD of each pixel unit $P_{m,n}$ of this specific range be output from the signal readout section 20. That is, where the row closest to the signal readout section 20 in the photodetecting section 10A is the first row as shown in FIG. 1, the controlling section 40A, when in the second imaging mode, preferably has a range from the first row to the $M_1$-th row in the photodetecting section 10A as the specific range, and makes a voltage value according to the amount of charges generated in the photodiode PD of each pixel unit $P_{m,n}$ of this specific range (first row to $M_1$-th row) be output from the signal readout section 20. This makes it highly likely, even with the n-th column readout wiring $L_{O,n}$ disconnected, to allow making a voltage value according to the amount of charges generated in the photodiode PD of each pixel unit $P_{m,n}$ of the specific range be normally output from the signal readout section 20 when in the second imaging mode.

The controlling section 40A preferably differentiates the gain being a ratio of an output voltage value to an input charge amount in the signal readout section 20 between the first imaging mode and second imaging mode. That is, when each integrating circuit $S_n$ is configured as shown in FIG. 3, it is preferable that the controlling section 40A, by controlling to open and close the gain setting switch $SW_{22}$ by the gain setting signal Gain, appropriately sets the capacitance value of the feedback capacitance section of each integrating circuit $S_n$ to differentiate the gain between the first imaging mode and second imaging mode. This allows, when, for example, the number of frames of data to be output per unit time from the signal readout section 20 (frame rate) is different between the first imaging mode and second imaging mode, or performing binning readout for combining data of a plurality of pixel units into one pixel data in either of the first imaging mode and second imaging mode, the respective pixel data to have mutually close values between the first imaging mode and second imaging mode.

In such a case that, for example, the frame rate is higher when in the second imaging mode than when in the first imaging mode, or performing binning readout when in the first imaging mode, it is preferable that the gain when in the second imaging mode is greater than when in the first imaging mode. Therefore, when in the first imaging mode, the controlling section 40A closes the gain setting switch $SW_{22}$ to thereby make the capacitance value of the feedback capacitance section equal to a sum of the respective capacitance values of the integrating capacitor $C_{21}$ and integrating capacitor $C_{22}$. On the other hand, when in the second imaging mode, the controlling section 40A opens the gain setting switch $SW_{22}$ to thereby make the capacitance value of the feedback capacitance section equal to the capacitance value of the integrating capacitor $C_{21}$. In this way, when in the second imaging mode than when in the first imaging mode, the capacitance value of the feedback capacitance section of each integrating circuit $S_n$ can be made smaller to make the gain larger. This allows, between the first imaging mode and second imaging mode, the respective pixel data to have mutually close values.

Next, operation of the solid-state image pickup apparatus 1A according to the first embodiment will be described. In the solid-state image pickup apparatus 1A according to the present embodiment, as a result of level changes of each of the M row selection control signals Vsel(1) to Vsel(M), the N column selection control signals Hsel(1) to Hsel(N), the reset control signal Reset, and the hold control signal Hold at predetermined timings under control by the controlling section 40A, light made incident on the photodetecting section 10A can be imaged to obtain frame data.

Figure 4:
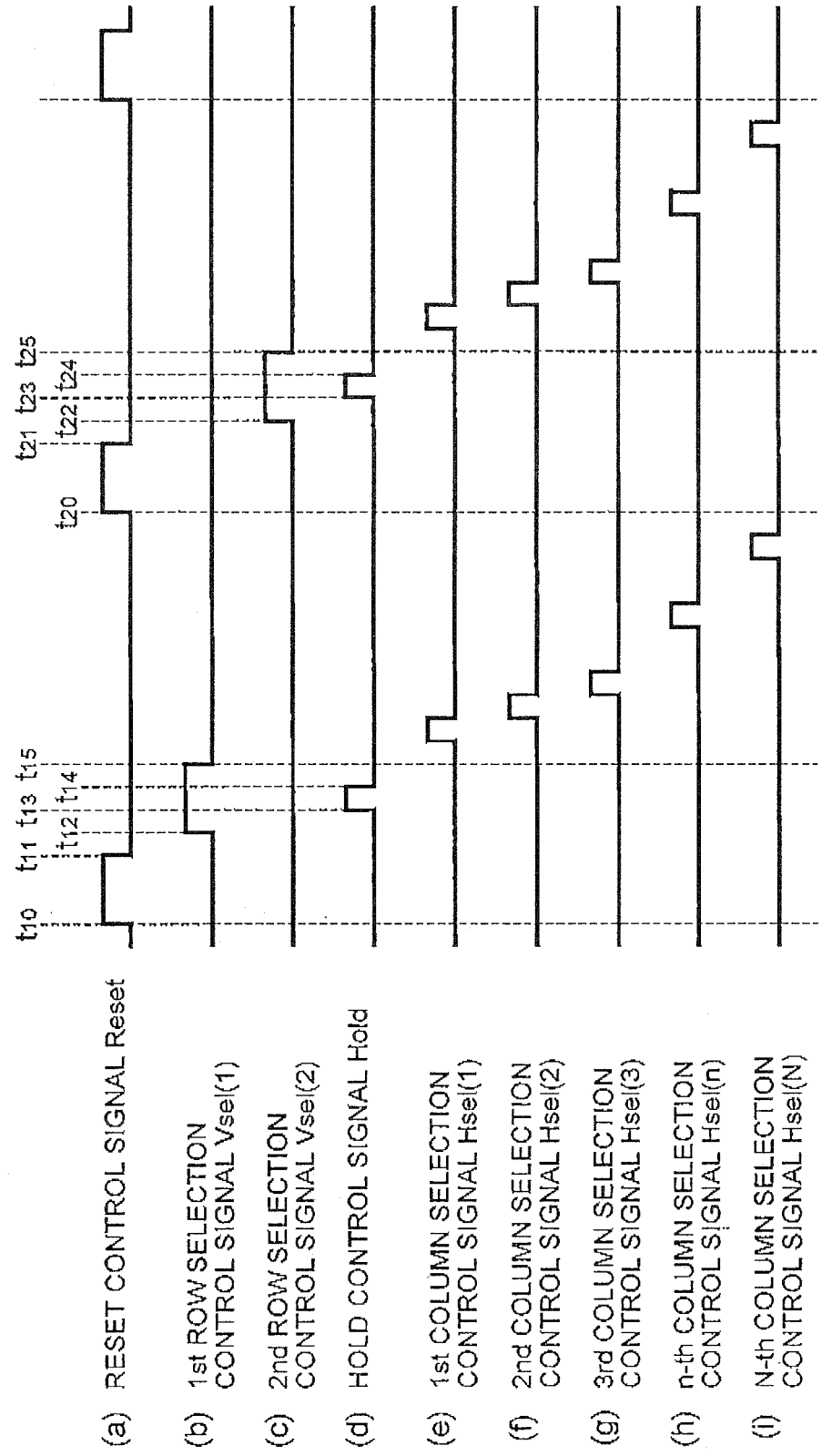
FIG. 4 is a timing chart for explaining operation of the solid-state image pickup apparatus 1A according to the first embodiment.

FIG. 4 is a timing chart for explaining operation of the solid-state image pickup apparatus 1A according to the first embodiment. In addition, description will be given here of the operation when not performing binning readout. This figure shows, in order from the top, (a) the reset control signal Reset for instructing an opening and closing operation of the discharging switch $SW_{21}$ in each of the N integrating circuits $S_1$ to $S_N$, (b) the first row selection control signal Vsel(1) for instructing an opening and closing operation of the readout switch $SW_1$ in each of the N pixel units $P_{1,1}$ to $P_{1,N}$ of the first row in the photodetecting section 10A, (c) the second row selection control signal Vsel(2) for instructing an opening and closing operation of the readout switch $SW_1$ in each of the N pixel units $P_{2,1}$ to $P_{2,N}$ of the second row in the photodetecting section 10A, and (d) the hold control signal Hold for instructing an opening and closing operation of the input switch $SW_{31}$ in each of the N holding circuits $H_1$ to $H_N$.

Moreover, this figure further goes on to show, in order, (e) the first column selection control signal Hsel(1) for instructing an opening and closing operation of the output switch $SW_{32}$ of the holding circuit $H_1$, (f) the second column selection control signal Hsel(2) for instructing an opening and closing operation of the output switch $SW_{32}$ of the holding circuit $H_2$, (g) the third column selection control signal Hsel(3) for instructing an opening and closing operation of the output switch $SW_{32}$ of the holding circuit $H_3$, (h) the n-th column selection control signal Hsel(n) for instructing an opening and closing operation of the output switch $SW_{32}$ of the holding circuit IL, and (i) the N-th column selection control signal Hsel(N) for instructing an opening and closing operation of the output switch $SW_{32}$ of the holding circuit $H_N$.

Charges generated in the photodiode PD of each of the N pixel units $P_{1,1}$ to $P_{1,N}$ of the first row and accumulated in the junction capacitance section of the photodiode PD itself are read out as follows. Before the time $t_{10}$, each of the M row selection control signals Vsel(1) to Vsel(M), the N column selection control signals Hsel(1) to Hsel(N), the reset control signal Reset, and the hold control signal Hold is at low level.

During a period from the time $t_{10}$ to the time $t_{11}$, the reset control signal Reset to be output from the controlling section 40A to the reset wiring $L_R$ becomes high level, and accordingly, in each of the N integrating circuits $S_1$ to $S_N$, the discharging switch $SW_{21}$ closes, and the integrating capacitor $C_{21}$ is discharged. Moreover, during a period from the time $t_{12}$ to the time $t_{15}$ after the time $t_{11}$, the first row selection control signal Vsel(1) to be output from the controlling section 40A to the first row selecting wiring $L_{V,1}$ becomes high level, and accordingly, the readout switch $SW_1$ in each of the N pixel units $P_{1,1}$ to $P_{1,N}$ of the first row in the photodetecting section 10A closes.

In this period ($t_{12}$ to $t_{15}$), during a period from the time $t_{13}$ to the time $t_{14}$, the hold control signal Hold to be output from the controlling section 40A to the holding wiring $L_H$ becomes high level, and accordingly, the input switch $SW_{31}$ closes in each of the N holding circuits $H_1$ to $H_N$.

In the period ($t_{12}$ to $t_{15}$), the readout switch $SW_1$ in each pixel unit $P_{1,n}$ of the first row is closed, and the discharging switch $SW_{21}$ of each integrating circuit $S_n$ is open, and thus charges generated in the photodiode PD of each pixel unit $P_{1,n}$ and accumulated in the junction capacitance section of the photodiode PD itself until then are transferred to and accumulated in the integrating capacitor $C_{21}$ of the integrating circuit $S_n$ through the readout switch $SW_1$ of the pixel unit $P_{1,n}$ and the n-th column readout wiring $L_{O,n}$. Then, a voltage value according to the amount of charges accumulated in the integrating capacitor $C_{21}$ of each integrating circuit $S_n$ is output from the output terminal of the integrating circuit $S_n$.

At the time $t_{14}$ in the period ($t_{12}$ to $t_{15}$), as a result of the hold control signal Hold switching from high level to low level, in each of the N holding circuits $H_1$ to $H_N$, the input switch $SW_{31}$ switches from a closed state to an open state, and a voltage value being output from the output terminal of the integrating circuit $S_n$ and being input to the input terminal of the holding circuit $H_n$ at this time is held in the holding capacitor $C_3$.

Then, after the period ($t_{12}$ to $t_{15}$), column selection control signals Hsel(1) to Hsel(N) to be output from the controlling section 40A to the column selecting wirings $L_{H,1}$ to $L_{H,N}$ sequentially become high level for a predetermined period, and accordingly, the output switches $SW_{32}$ in the N holding circuits $H_1$ to $H_N$ sequentially close for the predetermined period, the voltage values held in the holding capacitors $C_3$ of the holding circuits $H_n$ are sequentially output to the voltage outputting wiring $L_{out}$ through the output switches $SW_{32}$. The voltage value $V_{out}$ to be output to the voltage outputting wiring $L_{out}$ indicates a received light intensity in the photodiode PD of each of the N pixel units $P_{1,1}$ to $P_{1,N}$ of the first row.

Subsequently, charges generated in the photodiode PD of each of the N pixel units $P_{2,1}$ to $P_{2,N}$ of the second row and accumulated in the junction capacitance section of the photodiode PD itself are read out as follows.

During a period from the time $t_{20}$ to the time $t_{21}$, the reset control signal Reset to be output from the controlling section 40A to the reset wiring $L_R$ becomes high level, and accordingly, in each of the N integrating circuits $S_1$ to $S_N$, the discharging switch $SW_{21}$ closes, and the integrating capacitor $C_{21}$ is discharged. Moreover, during a period from the time $t_{22}$ to the time $t_{25}$ after the time $t_{21}$, the second row selection control signal Vsel(2) to be output from the controlling section 40A to the second row selecting wiring $L_{V,2}$ becomes high level, and accordingly, the readout switch $SW_1$ in each of the N pixel units $P_{2,1}$ to $P_{2,N}$ of the second row in the photodetecting section 10A closes.

In this period ($t_{22}$ to $t_{25}$), during a period from the time $t_{23}$ to the time $t_{24}$, the hold control signal Hold to be output from the controlling section 40A to the holding wiring $L_H$ becomes high level, and accordingly, the input switch $SW_{31}$ closes in each of the N holding circuits $H_1$ to $H_N$.

Then, after the period ($t_{22}$ to $t_{25}$), column selection control signals Hsel(1) to Hsel(N) to be output from the controlling section 40A to the column selecting wirings $L_{H,1}$ to $L_{H,N}$ sequentially become high level for a predetermined period, and accordingly, the output switches $SW_{32}$ in the respective N holding circuits $H_1$ to $H_N$ sequentially close for the predetermined period. Thus, the voltage value $V_{out}$ indicating a received light intensity in the photodiode PD of each of the N pixel units $P_{2,1}$ to $P_{2,N}$ of the second row is output to the voltage outputting wiring $L_{out}$.

When in the first imaging mode, subsequent to the operation for the first and the second rows as in the above, the same operation is performed for the third to the M-th rows, so that frame data indicating an image captured in one time of imaging is obtained. When the operation is completed for the M-th row, the same operation is again performed in a range from the first row to the M-th row, and frame data indicating a next image is obtained. By thus repeating the same operation with a predetermined period, voltage values $V_{out}$ indicating a two-dimensional intensity distribution of an image of light received by the photodetecting section 10A are output to the voltage outputting wiring $L_{out}$, and the frame data is repeatedly obtained.

Figure 5:
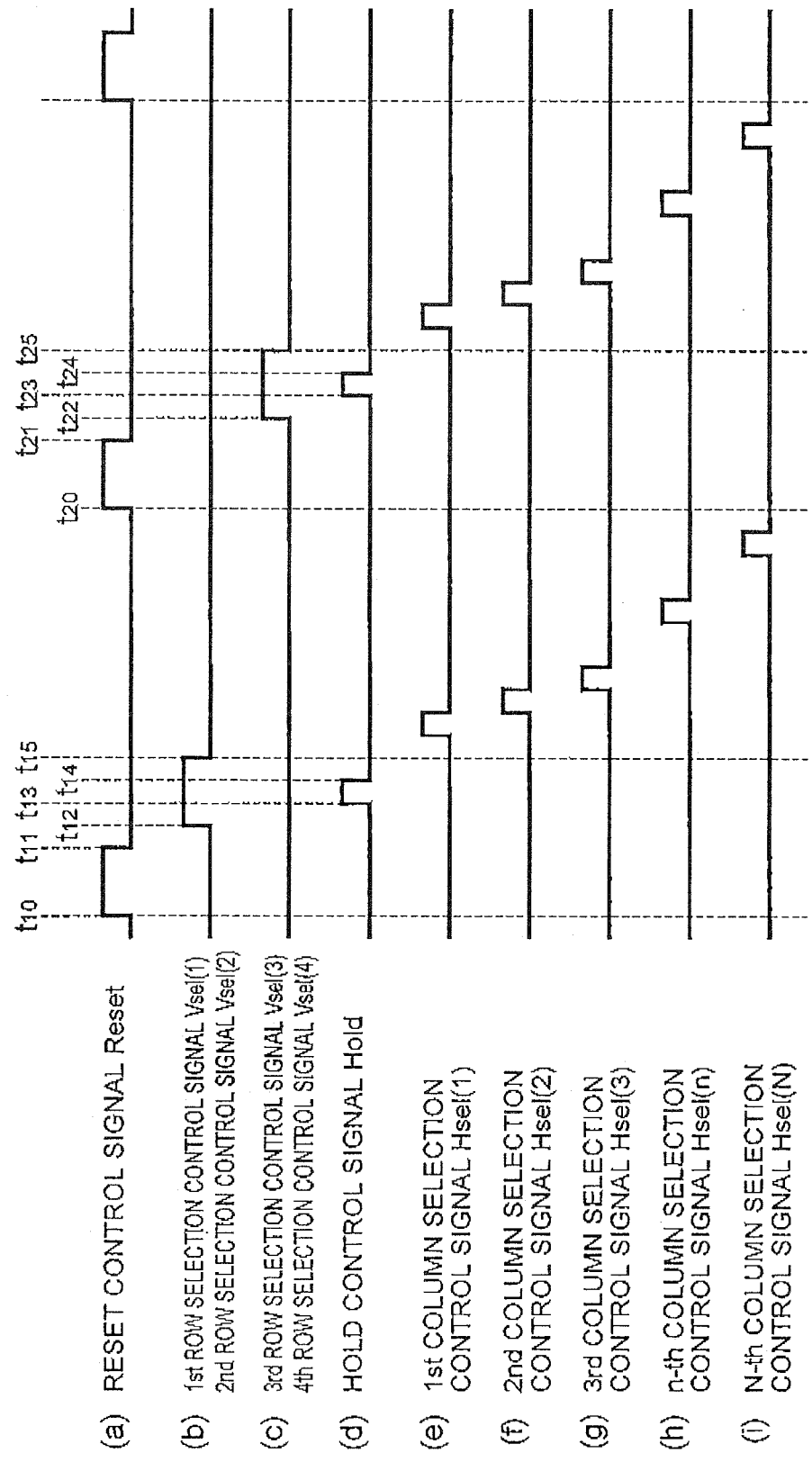
FIG. 5 is a timing chart for explaining operation of the solid-state image pickup apparatus 1A according to the first embodiment.

In addition, the solid-state image pickup apparatus 1A according to the present embodiment, in the case of binning readout when in the first imaging mode, performs the operation as shown in FIG. 5. FIG. 5 is a timing chart for explaining operation of the solid-state image pickup apparatus 1A according to the first embodiment. This figure shows the operation in the case of binning readout of 2 rows and 2 columns, that is, the operation when the readout pixel pitch in the frame data is set to two times the pitch of the pixel units. Also, in the case of binning readout, it is preferable in each integrating circuit $S_n$ that the gain setting switch $SW_{22}$ is closed, and the capacitance value of the feedback capacitance section is set to a larger value to make the gain smaller.

This figure shows, in order from the top, (a) the reset control signal Reset, (b) the first row selection control signal Vsel(1) and the second row selection control signal Vsel(2), (c) the third row selection control signal Vsel(3) and the fourth row selection control signal Vsel(4), (d) the hold control signal Hold, (e) the first column selection control signal Hsel(1), (f) the second column selection control signal Hsel(2), (g) the third column selection control signal Hsel(3), (h) the n-th column selection control signal Hsel(n), and (i) the N-th column selection control signal Hsel(N).

In the case of binning readout of 2 rows and 2 columns, as shown in this figure, during a period from the time $t_{12}$ to the time $t_{15}$, the first row selection control signal Vsel(1) to be output from the controlling section 40A to the first row selecting wiring $L_{V,1}$ becomes high level, and the readout switch $SW_1$ in each of the N pixel units $P_{1,1}$ to $P_{1,N}$ of the first row in the photodetecting section 10A closes. Moreover, during the same period, the second row selection control signal Vsel(2) to be output from the controlling section 40A to the second row selecting wiring $L_{V,2}$ becomes high level, and the readout switch $SW_1$ in each of the N pixel units $P_{2,1}$ to $P_{2,N}$ of the second row in the photodetecting section 10A closes.

Accordingly, charge generated in the photodiode PD of each of the pixel unit $P_{1,n}$ and pixel unit $P_{2,n}$ and accumulated in the junction capacitance section of the photodiode PD itself are transferred to and accumulated in the integrating capacitors $C_{21}$, $C_{22}$ of the integrating circuit $S_n$ through the readout switch $SW_1$ of each pixel unit and the n-th column readout wiring $L_{O,n}$. Then, a voltage value according to the amount of charges accumulated in the integrating capacitors $C_{21}$, $C_{22}$ of each integrating circuit $S_n$ is output from the output terminal of the integrating circuit $S_n$. The operation of each of the N integrating circuits $S_1$ to $S_N$ and the N holding circuits $H_1$ to $H_N$ is the same as the foregoing.

The voltage values sequentially output from the respective N holding circuits $H_1$ to $H_N$ are input to the A/D converting section 30, and converted to digital values according to the input voltage values. Then, of the N digital values output from the A/D converting section 30, digital values corresponding to each of the first and the second columns are added, and the following digital values are continuously added two by two.

In the same manner, during a period from the time $t_{22}$ to the time $t_{25}$, the third row selection control signal Vsel(3) to be output from the controlling section 40A to the third row selecting wiring $L_{V,3}$ becomes high level, and the readout switch $SW_1$ in each of the N pixel units $P_{3,1}$ to $P_{3,N}$ of the third row in the photodetecting section 10A closes. Moreover, during the same period, the fourth row selection control signal Vsel(4) to be output from the controlling section 40A to the fourth row selecting wiring $L_{V,4}$ becomes high level, and the readout switch $SW_1$ in each of the N pixel units $P_{4,1}$ to $P_{4,N}$ of the fourth row in the photodetecting section 10A closes. The same processing is performed in the signal readout section 20 and the A/D converting section 30. Then, of the N digital values output from the A/D converting section 30, digital values corresponding to each of the first and the second columns are added, and the following digital values are continuously added two by two.

Thus, as a result of the processing being simultaneously performed for two rows each time in order from the first row in the photodetecting section 10A, and the N digital values output from the A/D converting section 30 are added in order two by two, binning readout of two rows and two columns can be performed.

On the other hand, when in the second imaging mode, the same operation is performed in the range from the first row to the $M_1$-th row as in the above, so that frame data indicating an image captured in one time of imaging is obtained. When the operation is completed for the $M_1$-th row, the same operation is again performed in a range from the first row to the $M_1$-th row, and frame data indicating a next image is obtained. By thus repeating the same operation with a predetermined period, voltage values $V_{out}$ indicating a two-dimensional intensity distribution of an image of light received by the photodetecting section 10A are output to the voltage outputting wiring $L_{out}$, and the frame data is repeatedly obtained.

When in the second imaging mode, output of a voltage value from the signal readout section 20 to the voltage outputting wiring $L_{out}$ is not performed in terms of a range from the ($M_1$+1)-th row to the M-th row. However, also in each pixel unit $P_{m,n}$ of the range from the ($M_1$+1)-th row to the M-th row, charges generated in response to light incidence into the photodiode PD are accumulated in the junction capacitance section of the photodiode PD, and exceed a saturation level of the junction capacitance section over time. If the amount of charges accumulated in the junction capacitance section of the photodiode PD exceeds the saturation level, a surplus of charges over the saturation level overflows to neighboring pixel units. If the neighboring pixel units belong to the $M_1$-th row, voltage values to be output from the signal readout section 20 to the voltage outputting wiring $L_{out}$ in terms of the neighboring pixel units are incorrect.

Therefore, it is favorable to provide discharging means for discharging the junction capacitance section of the photodiode PD in each pixel unit of the range from the ($M_1$+1)-th row to the M-th row when in the second imaging mode. The solid-state image pickup apparatus 1A according to the present embodiment performs, as such discharging means, the operation as shown in FIG. 6 when in the second imaging mode to transfer to the integrating circuit $S_n$ the charges accumulated in the junction capacitance section of the photodiode PD in each pixel unit $P_{m,n}$ of the range from the $(M_1+1)$-th row to the M-th row, thereby discharging the junction capacitance section of the photodiode PD.

Figure 6:
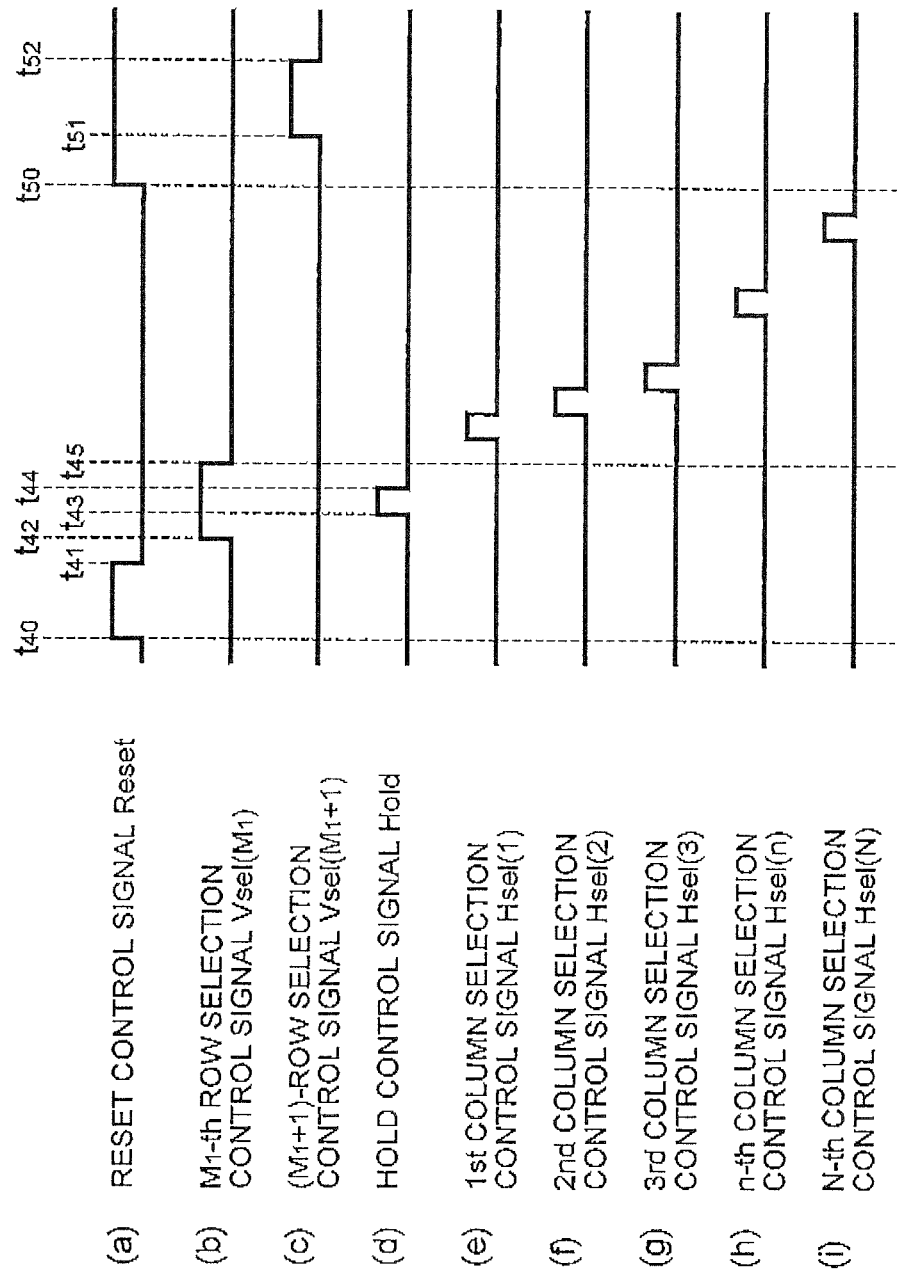
FIG. 6 is a timing chart for explaining operation of the solid-state image pickup apparatus 1A according to the first embodiment.

FIG. 6 is a timing chart for explaining operation of the solid-state image pickup apparatus 1A according to the first embodiment. This figure shows the operation for each of the $M_1$-th and the $(M_1+1)$-th rows in the second imaging mode.

This figure shows, in order from the top, (a) the reset control signal Reset, (b) the $M_1$-th row selection control signal Vsel($M_1$), (c) the $(M_1+1)$-th row selection control signal Vsel($M_1+1$), (d) the hold control signal Hold, (e) the first column selection control signal Hsel(1), (f) the second column selection control signal Hsel(2), (g) the third column selection control signal Hsel(3), (h) the n-th column selection control signal Hsel(n), and (i) the N-th column selection control signal Hsel(N).

The operation for the $M_1$-th row in the period from the time $t_{40}$ to the time $t_{50}$ shown in FIG. 6 is the same as the operation for the first row in the period from the time $t_{10}$ to the time $t_{20}$ shown in FIG. 4. However, during a period from the time $t_{42}$ to the time $t_{45}$, the $M_1$-th row selection control signal Vsel ($M_1$) to be output from the controlling section 40A to the $M_1$-th row selecting wiring $L_{V,M1}$ becomes high level, and accordingly, the readout switch $SW_1$ in each of the N pixel units $P_{M1,1}$ to $P_{M1,N}$ of the $M_1$-th row in the photodetecting section 10A closes.

When the operation for the $M_1$-th row is completed when in the second imaging mode, from the time $t_{50}$ onward, the operation for the range from the $(M_1+1)$-th row to the M-th row is performed. That is, from the time $t_{50}$ onward, the reset control signal Reset to be output from the controlling section 40A to the reset wiring $L_R$ becomes high level, and accordingly, in each of the N integrating circuits $S_1$ to $S_N$, the discharging switch $SW_{21}$ closes. Moreover, during a period from the time $t_{50}$ onward where the discharging switch $SW_{21}$ is closed, the $(M_1+1)$-th row to the M-th row selection control signals Vsel($M_1+1$) to Vsel(M) become high level, and accordingly, the readout switch $SW_1$ in each pixel unit $P_{m,n}$ of the range from the $(M_1+1)$-th row to the M-th row in the photodetecting section 10A closes.

Thus, as a result of the readout switch $SW_1$ in each pixel unit $P_{m,n}$ of the range from the $(M_1+1)$-th row to the M-th row closing when in the second imaging mode, the charges accumulated in the junction capacitance section of the photodiode PD in the pixel unit are transferred to the integrating circuit $S_n$, and as a result of the discharging switch $SW_{21}$ closing in each integrating circuit $S_n$, the integrating capacitor $C_{21}$ of each integrating circuit $S_n$ is always in a discharged state. In this way, the junction capacitance section of the photodiode PD in each pixel unit $P_{m,n}$ of the range from the $(M_1+1)$-th row to the M-th row can be discharged when in the second imaging mode.

At this time, in terms of the range from the $(M_1+1)$-th row to the M-th row, the row selection control signals Vsel($M_1+1$) to Vsel(M) may sequentially become high level, but a plurality of row selection control signals of the row selection control signals Vsel($M_1+1$) to Vsel(M) may simultaneously become high level, and all of the row selection control signals Vsel($M_1+1$) to Vsel(M) may simultaneously become high level. Thus, in terms of the range from the $(M_1+1)$-th row to the M-th row, as a result of a plurality or all of the row selection control signals simultaneously becoming high level, the junction capacitance section of the photodiode PD in each pixel unit $P_{m,n}$ can be discharged in a shorter time.

Meanwhile, it can also be considered, as another imaging mode for outputting data of a smaller number of pixel units than in the first imaging mode from the signal readout section 20, to output a voltage value according to the amount of charge generated in the photodiode PD of each pixel unit $P_{m,n}$ included in consecutive $N_1$ columns in the photodetecting section 10A from the signal readout section 20. Here, $N_1$ is an integer less than N. However, in the imaging mode for thus outputting data of each pixel unit $P_{m,n}$ of the $N_1$ columns from the signal readout section 20, it is necessary to output the M row selection control signals Vsel(1) to Vsel(M) from the controlling section 40A in order to obtain one frame of data. In contrast thereto, the solid-state image pickup apparatus 1A according to the present embodiment, for which, it suffices, when in the second imaging mode for outputting data of each pixel unit $P_{m,n}$ of the $M_1$ rows from the signal readout section 20, to output $M_1$ row selection control signals Vsel(1) to Vsel($M_1$) from the controlling section 40A in order to obtain one frame of data, can thus perform a high-speed operation.

In addition, in the timing charts shown in FIG. 4 to FIG. 6 described thus far, each integrating circuit $S_n$ is initialized after readout of a voltage value from each holding circuit $H_n$ is completed. However, if after an output voltage value of each integrating circuit $S_n$ is held by the holding circuit $H_n$, the reset control signal Reset may be made high level to initialize each integrating circuit $S_n$ during a period of reading out a voltage value from each holding circuit $H_n$. This allows a higher-speed operation.

Figure 7:
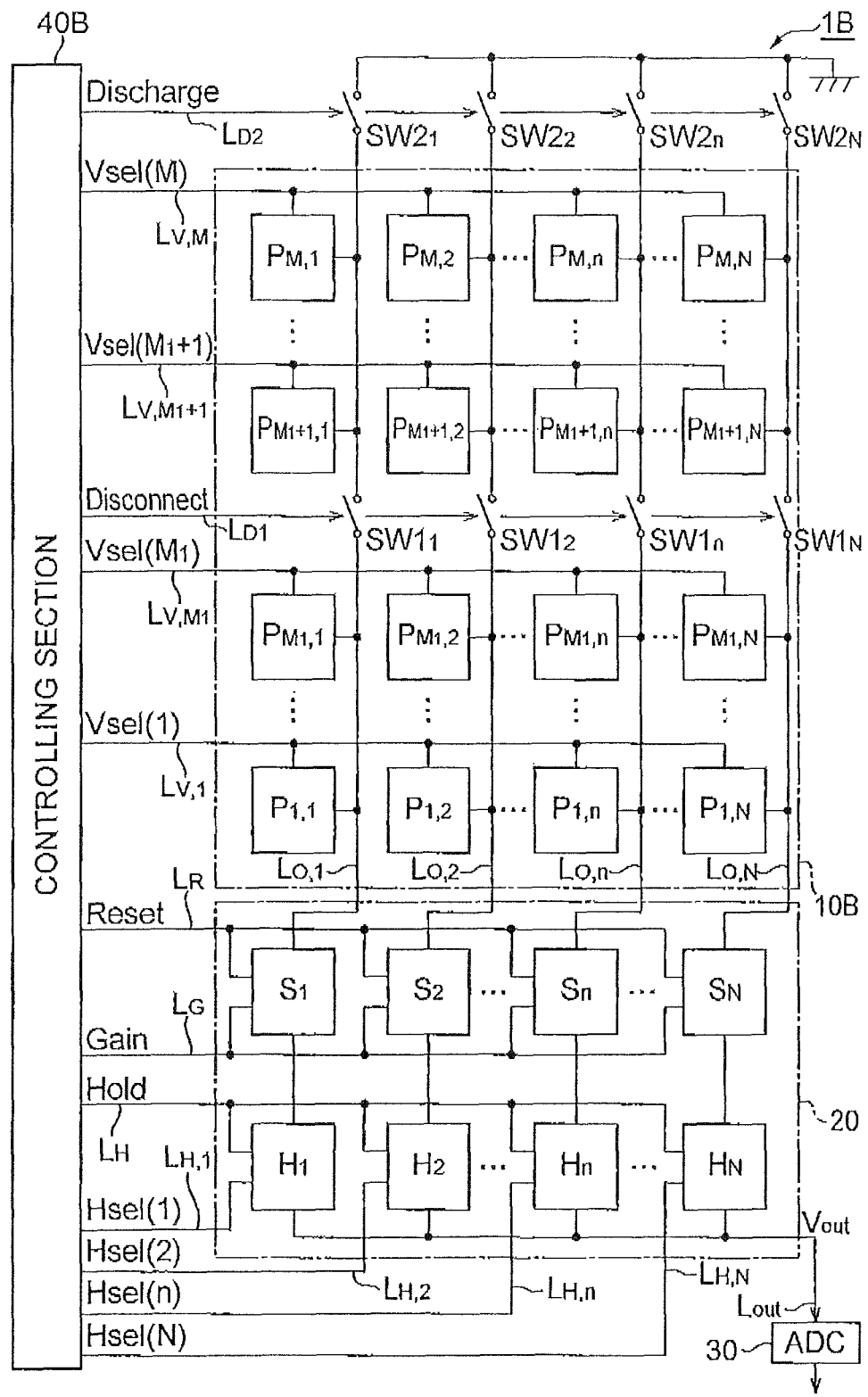
FIG. 7 is a view showing a configuration of a solid-state image pickup apparatus 1B according to a second embodiment.

Next, description will be given of a solid-state image pickup apparatus 1B according to a second embodiment. FIG. 7 is a view showing a configuration of the solid-state image pickup apparatus 1B according to the second embodiment. The solid-state image pickup apparatus 1B shown in this figure includes a photodetecting section 10B, a signal readout section 20, an A/D converting section 30, and a controlling section 40B. Moreover, in the case of use as one for X-ray detection, a scintillator section is provided so as to cover the photodetecting section 10B of the solid-state image pickup apparatus 1B.

As compared with the configuration of the solid-state image pickup apparatus 1A according to the first embodiment shown in FIG. 1, the solid-state image pickup apparatus 1B according to the second embodiment shown in FIG. 7 is different in that a disconnecting switch $SW1_n$ and a discharging switch $SW2_n$ are provided on each n-th column readout wiring $L_{O,n}$, and is different in including a controlling section 40B in place of the controlling section 40A.

Each disconnecting switch $SW1_n$ is provided, on the readout wiring $L_{O,n}$, between the $M_1$-th row and the $(M_1+1)$-th row in the photodetecting section 10B. That is, when the disconnecting switch $SW1_n$ is closed, each pixel unit $P_{m,n}$ in a range from the first row to the M-th row is connected via the readout wiring $L_{O,n}$ with the signal readout section 20. On the other hand, when the disconnecting switch $SW1_n$ is open, each pixel unit $P_{m,n}$ in a range from the first row to the $M_1$-th row are connected via the readout wiring $L_{O,n}$ with the signal readout section 20, but each pixel unit $P_{m,n}$ in a range from the $(M_1+1)$-th, row to the M-th row are disconnected from the signal readout section 20. Each disconnecting switch $SW1_n$ is connected via a disconnection wiring $L_{D1}$ with the controlling section 40B, and supplied with a disconnection control signal Disconnect passed through the disconnection wiring $L_{D1}$ from the controlling section 40B. The disconnection control signal Disconnect is a signal for instructing an opening and closing operation of each disconnecting switch $SW1_n$.

Each discharging switch $SW2_n$ is provided, on the readout wiring $L_{O,n}$, at a side further distant from the signal readout section 20 than the position where the disconnecting switch $SW1_n$ is provided. One end of the discharging switch $SW2_n$ is connected, via the readout wiring $L_{O,n}$, with each pixel unit $P_{m,n}$ in the range from the $(M_1+1)$-th row to the M-th row. The other end of the discharging switch $SW2_n$ is grounded. Each discharging switch $SW2_n$ is connected via a discharge wiring $L_{D2}$ with the controlling section 40B, and supplied with a discharge control signal Discharge passed through the discharge wiring $L_{D2}$ from the controlling section 40B. The discharge control signal Discharge is a signal for instructing an opening and closing operation of each discharging switch $SW2_n$.

The controlling section 40B, in the same manner as the controlling section 40A in the first embodiment, outputs an m-th row selection control signal Vsel(m) to the m-th row selecting wiring $L_{V,m}$, outputs an n-th column selection control signal Hsel(n) to the n-th column selecting wiring $L_{H,n}$, outputs a discharge control signal Reset to the discharge wiring $L_R$, outputs a gain setting signal Gain to the gain setting wiring $L_G$, and outputs a hold control signal Hold to the holding wiring $L_H$.

In addition, the controlling section 40B outputs a disconnection control signal Disconnect to the disconnection wiring $L_{D1}$ to supply this disconnection control signal Disconnect to each of the N disconnecting switches $SW1_1$ to $SW1_N$. Moreover, the controlling section 40B outputs a discharge control signal Discharge to the discharge wiring $L_{D2}$ to supply this discharge control signal Discharge to each of the N discharging switches $SW2_1$ to $SW2_N$.

The solid-state image pickup apparatus 1B according to the second embodiment also has a first imaging mode and a second imaging mode. The first imaging mode and the second imaging mode are mutually different in an imaging region in the photodetecting section 10B. The controlling section 40B, when in the first imaging mode, makes a voltage value according to the amount of charges generated in the photodiode PD of each of the M×N pixel units $P_{1,1}$ to $P_{M,N}$ in the photodetecting section 10B be output from the signal readout section 20. Also, the controlling section 40B, when in the second imaging mode, makes a voltage value according to the amount of charges generated in the photodiode PD of each pixel unit $P_{m,n}$ of the range from the first row to the $M_1$-th row in the photodetecting section 10B be output from the signal readout section 20.

In the solid-state image pickup apparatus 1B according to the second embodiment, when in the first imaging mode, the disconnection control signal Disconnect to be supplied to each disconnecting switch $SW1_n$ through the disconnection wiring $L_{D1}$ from the controlling section 40B becomes high level, and each disconnecting switch $SW1_n$ closes. Moreover, the discharge control signal Discharge to be supplied to each discharging switch $SW2_n$ through the discharge wiring $L_{D2}$ from the controlling section 40B becomes low level, and each discharging switch $SW2_n$ opens. In this state, each pixel unit $P_{m,n}$ in the range from the first row to the M-th row are connected via the readout wiring $L_{O,n}$ with the signal readout section 20. Then, the same operation as in the case of the first embodiment is performed, whereby a voltage value according to the amount of charges generated in the photodiode PD of each of the M×N pixel units $P_{1,1}$ to $P_{M,N}$ in the photodetecting section 10B is output from the signal readout section 20.

On the other hand, in the solid-state image pickup apparatus 1B according to the second embodiment, when in the second imaging mode, the disconnection control signal Disconnect to be supplied to each disconnecting switch $SW1_n$ through the disconnection wiring $L_{D1}$ from the controlling section 40B becomes low level, and each disconnecting switch $SW1_n$ opens. Moreover, the discharge control signal Discharge to be supplied to each discharging switch $SW2_n$ through the discharge wiring $L_{D2}$ from the controlling section 40B becomes high level, and each discharging switch $SW2_n$ closes. In this state, each pixel unit in the range from the first row to the $M_1$-th row is connected via the readout wiring $L_{O,n}$ with the signal readout section 20, but each pixel unit $P_{m,n}$ in the range from the $(M_1+1)$-th row to the M-th row is disconnected from the signal readout section 20 and grounded.

Moreover, when in the second imaging mode, in terms of the range from the first row to the $M_1$-th row, the same operation as in the case of the first embodiment is performed, whereby a voltage value according to the amount of charges generated in the photodiode PD of each pixel unit is output from the signal readout section 20. On the other hand, in terms of the range from the $(M_1+1)$-th row to the M-th row, the row selection control signals $Vsel(M_1+1)$ to Vsel(M) become high level, and accordingly, the cathode terminal of the photo diode PD of each pixel unit $P_{m,n}$ is grounded via the readout switch $SW_1$ and the discharging switch $SW2_n$, and thus the junction capacitance section of the photodiode PD of each pixel unit $P_{m,n}$ is discharged. That is, in this case, each discharging switch $SW2_n$ acts as discharging means for discharging the junction capacitance section of the photodiode PD in each pixel unit $P_{m,n}$ of the range from the $(M_1+1)$-th row to the M-th row when in the second imaging mode.

When in the second imaging mode, in to ins of the range from the $(M_1+1)$-th row to the M-th row, the row selection control signals $Vsel(M_1+1)$ to Vsel(M) may sequentially become high level, but a plurality of row selection control signals of the row selection control signals $Vsel(M_1+1)$ to Vsel(M) may simultaneously become high level, and all of the row selection control signals $Vsel(M_1+1)$ to Vsel(M) may simultaneously become high level. Thus, in terms of the range from the $(M_1+1)$-th row to the M-th row, as a result of a plurality or all of the row selection control signals simultaneously becoming high level, the junction capacitance section of the photodiode PD in each pixel unit $P_{m,n}$ can be discharged in a shorter time.

Moreover, when in the second imaging mode, the period for which a voltage value according to the amount of charges generated in the photodiode PD of each pixel unit $P_{m,n}$ is output from the signal readout section 20 in terms of the range from the first row to the $M_1$-th row, and the period for which the junction capacitance section of the photodiode PD in each pixel unit $P_{m,n}$ is discharged in terms of the range from the $(M_1+1)$-th row to the M-th row may be partially overlapped with each other. In such a case, a higher-speed operation is possible.

Moreover, as a result of the disconnection wiring $L_{D1}$ being opened when in the second imaging mode, the n-th column readout wiring $L_{O,n}$ to be connected to the signal readout section 20 is shortened, and thus noise can be reduced.

Figure 8:
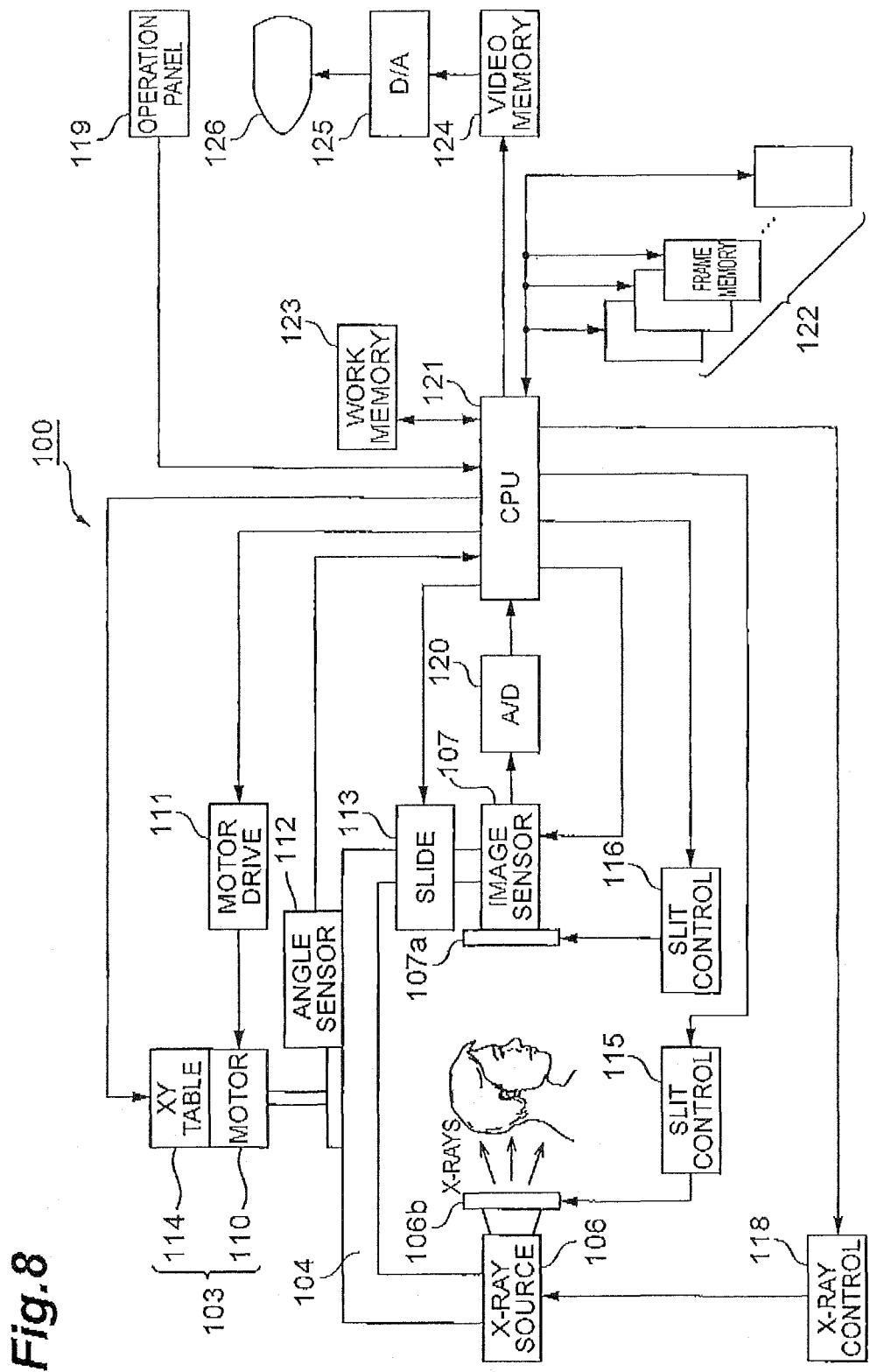
FIG. 8 is a configuration diagram of an X-ray inspection system 100 according to the present embodiment.

Next, description will be given of an embodiment of an X-ray inspection system including the solid-state image pickup apparatus according to the above embodiment. FIG. 8 is a configuration diagram of the X-ray inspection system 100 according to the present embodiment. The X-ray inspection system 100 according to the present embodiment includes the solid-state image pickup apparatus and an X-ray generator, and images X-rays output from the X-ray generator and transmitted through an inspection object by the solid-state image pickup apparatus to inspect the inspection object.

In the X-ray inspection system 100 shown in this figure, the X-ray generator 106 generates X-rays toward a subject (inspection object). The radiation field of X-rays generated from the X-ray generator 106 is controlled by a primary slit plate 106*b*. The X-ray generator 106 has an X-ray tube built therein, and by adjusting conditions of the X-ray tube, such as a tube voltage, a tube current, and energization time, the X-ray dose to the subject is controlled. An X-ray image sensor 107 has a built-in CMOS solid-state image pickup apparatus having a plurality of pixel units arrayed two-dimensionally, and detects an X-ray image transmitted through the subject. In front of the X-ray image sensor 107, a secondary slit plate 107*a* that limits an X-ray incident region is provided.

A swing arm 104 holds the X-ray generator 106 and the X-ray image sensor 107 so as to be opposed, and swings these around the subject in panoramic tomography. Moreover, in the case of linear tomography, a sliding mechanism 113 for linearly displacing the X-ray image sensor 107 with respect to the subject is provided. The swing arm 104 is driven by an arm motor 110 that forms a rotary table, and a rotation angle thereof is detected by an angle sensor 112. Moreover, the arm motor 110 is mounted on a movable portion of an XY table 114, and the center of rotation is arbitrarily adjusted in a horizontal plane.

Image signals output from the X-ray image sensor 107 are converted to, for example, 10-bit (=1024 level) digital data by an A/D converter 120, and once taken in a CPU (central processing unit) 121, and thereafter stored in a frame memory 122. From the image data stored in the frame memory 122, a tomographic image along any tomographic plane is reproduced by a predetermined arithmetic processing. The reproduced tomographic image is output to a video memory 124, and converted to analog signals by a D/A converter 125, and then displayed by an image display section 126 such as a CRT (cathode ray tube), and provided for various diagnoses.

The CPU 121 is connected with a work memory 123 required for signal processing, and further connected with an operation panel 119 having a panel switch, an X-ray irradiation switch, etc. Moreover, the CPU 121 is connected to a motor drive circuit 111 that drives the arm motor 110, slit control circuits 115, 116 that control the opening range of the primary slit plate 106*b* and the secondary slit plate 107*a*, an X-ray control circuit 118 that controls the X-ray generator 106, respectively, and further outputs a clock signal to drive the X-ray image sensor 107.

The X-ray control circuit 118 is capable of feedback-controlling the X-ray dose to the subject based on signals imaged by the X-ray image sensor 107.

In the X-ray inspection system 100 configured as above, the solid-state image pickup apparatus 1A or 1B according to the present embodiment is used as the X-ray image sensor 107.

The X-ray generator 106 can, as a result of the opening range of the slit plate 16*b* being controlled, output X-rays at a predetermined divergence angle when in a first output mode, and output X-rays at a narrower divergence angle than the predetermined divergence angle when in a second output mode. When the X-ray generator 106 outputs X-rays in the first output mode, the X-ray image sensor 107 being a solid-state image pickup apparatus operates in the first imaging mode. On the other hand, when the X-ray generator 106 outputs X-rays in the second output mode, the X-ray image sensor 107 being a solid-state image pickup apparatus operates in the second imaging mode.

Here, for example, the first output mode and the first imaging mode correspond to the CT mode described in Patent Document 1, and the second output mode and the second imaging mode correspond to the panoramic mode or cephalographic mode described in Patent Document 1. The solid-state image pickup apparatus 1A, 1B is disposed so that the longitudinal direction of an imaging region (the first row to the $M_1$-th row) in the photodetecting section 10A, 10B when in the second imaging mode is vertical to a swing plane.

The X-ray inspection system 100 according to the present embodiment includes the solid-state image pickup apparatus 1A or 1B according to the present embodiment, and can thus perform imaging at a high speed when in the second output mode and the second imaging mode.

In addition, assuming that the X-ray inspection system 100 including the solid-state image pickup apparatus 1A, 1B is used for a dental application, it is preferable that the number of rows M is larger than the number of columns N in the photodetecting section 10A, 10B of the solid-state image pickup apparatus 1A, 1B. This is attributed to the following reasons. That is, in the first imaging mode corresponding to the CT mode, a size of a light receiving range to be used for imaging in the photodetecting section 10A, 10B of, for example, 8 cm or more×12 cm or more is required. Moreover, in the second imaging mode corresponding to the panoramic mode, a size of a specific range to be used for imaging in the photodetecting section 10A, 10B of, for example, 15 cm or more×7 mm or more is required. In consideration of satisfying the requirements regarding the size as in the above and most efficiently preparing a single integrated solid-state image pickup apparatus 1A, 1B from a circular silicon wafer, the photodetecting section 10A, 10B cannot help but have a rectangular shape long in one direction. Therefore, on the assumption that the photodetecting section 10A, 10B cannot help but have a rectangular shape, the number of columns N is set larger than the number of rows M to reduce the number M of selection control signals to be output from the controlling section 40A, 40B. Moreover, it is preferable to separate the N holding circuits $H_1$ to $H_N$ in the signal readout section 20 into a plurality of sets, provide A/D converting sections individually for the sets, and make these A/D converting sections operate in parallel. This allows realizing a high-speed readout of pixel data.

Figure 9:
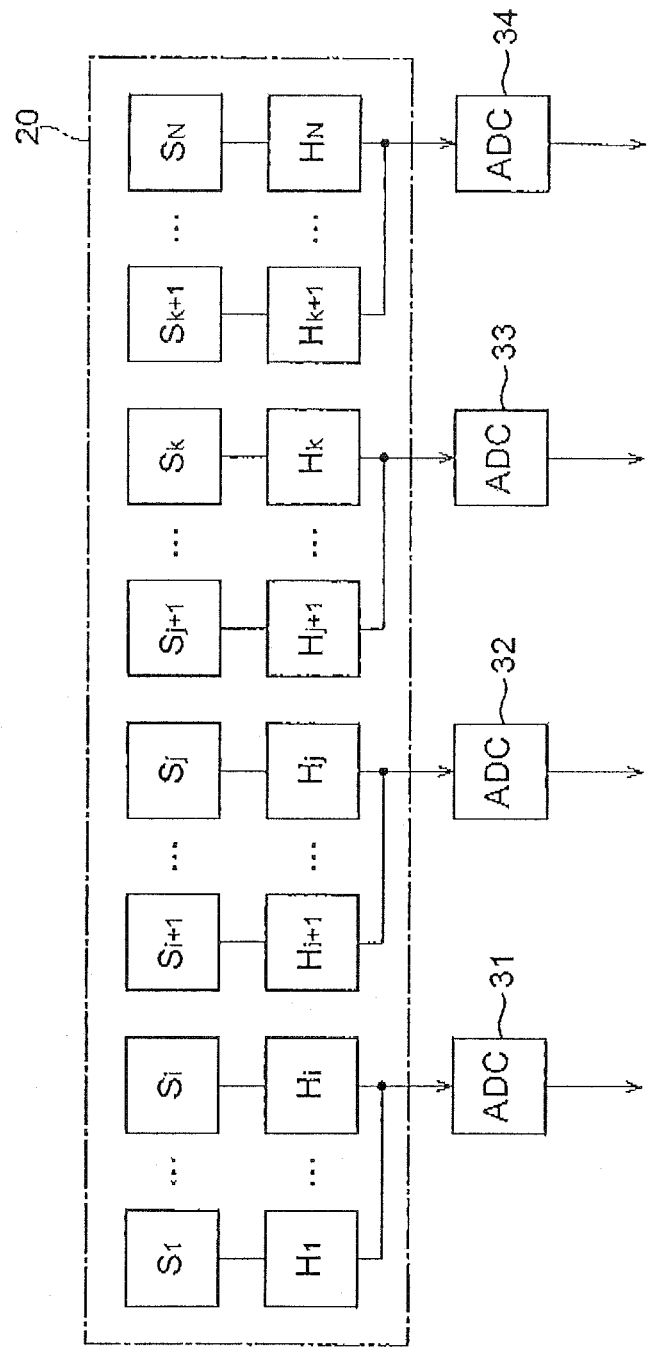
FIG. 9 is a view showing a modification of the configuration of the solid-state image pickup apparatus 1A, 1B according to the present embodiment.

For example, as shown in FIG. 9, the N integrating circuits $S_1$ to $S_N$ and the N holding circuits $H_1$ to $H_N$ are separated into four sets, where integrating circuits $S_1$ to $S_i$ and holding circuits $H_1$ to $H_i$ are provided as the first set, integrating circuits $S_{i+1}$ to $S_j$ and holding circuits $H_{i+1}$ to $H_j$ are provided as the second set, integrating circuits $S_{j+1}$ to $S_k$ and holding circuits $H_{j+1}$ to $H_k$ are provided as the third set, and integrating circuits $S_{k+1}$ to $S_N$ and holding circuits $H_{k+1}$ to $H_N$ are provided as the fourth set. Here, "1<i<j<k<N." Voltage values sequentially output from the first set of respective holding circuits $H_1$ to $H_i$ are converted to digital values by an A/D converting section 31, voltage values sequentially output from the second set of respective holding circuits $H_{i+1}$ to $H_j$ are converted to digital values by an A/D converting section 32, voltage values sequentially output from the third set of respective holding circuits $H_{j+1}$ to $H_k$ are converted to digital values by an A/D converting section 33, and voltage values sequentially output from the fourth set of respective holding circuits $H_{k+1}$ to $H_N$ are converted to digital values by an A/D converting section 34. Moreover, A/D converting in the respective four A/D converting sections 31 to 34 are performed in parallel. This allows realizing a high-speed readout of pixel data.

Moreover, in consideration of for example, binning readout of 2 rows and 2 columns, it is also preferable to provide holding circuits corresponding to odd-numbered columns out of the N holding circuits $H_1$ to $H_N$ as the first set, and holding circuits corresponding to even-numbered columns, as the second set, provide A/D converting sections individually for these first and second sets, respectively, and make these two A/D converting sections operate in parallel. In this case, voltage values are simultaneously output from the holding circuit corresponding to an odd-numbered column and a holding circuit corresponding to an even-numbered column neighboring the odd-numbered column, and these two voltage values are simultaneously A/D converted into digital values. Then, in the case of binning, these two digital values are added. This also allows realizing a high-speed readout of pixel data.

INDUSTRIAL APPLICABILITY

The present invention relates to a solid-state image pickup apparatus and an X-ray inspection system.

REFERENCE SIGNS LIST 1A, 1B Solid-state image pickup apparatus
10A, 10B Photodetecting section
20 Signal readout section
30 A/D converting section
40A, 40B Controlling section
$P_{1,1}$ to $P_{M,N}$ Pixel unit
PD Photodiode
$SW_1$ Readout switch
$SW1_1$ to $SW1_N$ Disconnecting switch
$SW2_1$ to $SW2_N$ Discharging switch
$S_1$ to $S_N$ Integrating circuit
$C_{21}$, $C_{22}$ Integrating capacitor
$SW_{21}$ Discharging switch
$A_2$ Amplifier
$H_1$ to $H_N$ Holding circuit
$C_3$ Holding capacitor
$SW_{31}$ Input switch
$SW_{32}$ Output switch
$L_{V,m}$ m-th row selecting wiring
$L_{H,n}$ n-th column selecting wiring
$L_{O,n}$ n-th column readout wiring
$L_R$ Reset wiring
$L_G$ Gain setting wiring
$L_H$ Holding wiring
$L_{out}$ Voltage outputting wiring

The invention claimed is:

1. A solid-state image pickup apparatus comprising: where M and N are each an integer not less than 2, $M_1$ is an integer less than M, m is an integer not less than 1 and not more than M, and n is an integer not less than 1 and not more than N, a photodetecting section having M×N pixel units $P_{1,1}$ to $P_{M,N}$ two-dimensionally arranged in M rows and N columns, each of the pixel units including a photodiode and a readout switch connected with the photodiode, the photodiode generating charges corresponding to an intensity of an incident light, a readout wiring $L_{O,n}$ connected with a readout switch of each of the M pixel units $P_{1,n}$ to $P_{M,n}$ of an n-th column in the photodetecting section, for reading out charges generated in the photodiode of any pixel unit of the M pixel units $P_{1,n}$ to $P_{M,n}$ via the readout switch of the pixel unit;

a signal readout section connected with each of the readout wirings $L_{O,1}$ to $L_{O,N}$, for holding a voltage value according to an amount of charges input through the readout wiring $L_{O,n}$, and sequentially outputting the held voltage values; and a controlling section that controls an opening and closing operation of the readout switch of each of the M×N pixel units $P_{1,1}$ to $P_{M,N}$ in the photodetecting section and controls an output operation of a voltage value in the signal readout section to make a voltage value according to an amount of charges generated in the photodiode of each of the M×N pixel units $P_{1,1}$ to $P_{M,N}$ in the photodetecting section be output from the signal readout section, wherein the controlling section when in a first imaging mode, makes a voltage value according to an amount of charges generated in the photodiode of each of the M×N pixel units $P_{1,1}$ to $P_{M,N}$ in the photodetecting section be output from the signal readout section, and when in a second imaging mode, makes a voltage value according to an amount of charges generated in the photodiode of each pixel unit $P_{m,n}$ included in a specific range of consecutive $M_1$ rows in the photodetecting section be output from the signal readout section, wherein the controlling section, when in the second imaging mode, has as the specific range, a range of $M_1$ rows counted in order from the row closest to the signal readout section out of the M rows in the photodetecting section, and makes a voltage value according to the amount of charges generated in the photodiode of each pixel unit $P_{m,n}$ in the specific range be output from the signal readout section, the solid-state image pickup apparatus further comprising, between the specific range in the photodetecting section and another range excluding the specific range, a disconnecting switch provided on each readout wiring $L_{O,n}$, wherein the controlling section closes the disconnecting switch when in the first imaging mode, and opens the disconnecting switch when in the second imaging mode.

2. The solid-state image pickup apparatus according to claim 1, including discharging means that discharges a junction capacitance section of the photodiode in each pixel unit $P_{m,n}$ of another range excluding the specific range in the photodetecting section when in the second imaging mode.

3. The solid-state image pickup apparatus according to claim 1, wherein the controlling section differentiates a gain being a ratio of an output voltage value to an input charge amount in the signal readout section between the first imaging mode and second imaging mode.

4. The solid-state image pickup apparatus according to claim 1, further comprising a scintillator section that is provided so as to cover the M×N pixel units $P_{1,1}$ to $P_{M,N}$ in the photodetecting section.

5. An X-ray inspection system including the solid-state image pickup apparatus according to claim 4 and an X-ray generator, which images X-rays output from the X-ray generator and transmitted through an inspection object by the solid-state image pickup apparatus to inspect the inspection object.

6. A solid-state image pickup apparatus comprising:

a photodetecting section having M×N pixel units $P_{1,1}$ to $P_{M,N}$ two-dimensionally arranged in M rows and N columns, where M and N are each an integer not less than 2, each of the pixel units including a photodiode and a readout switch connected with the photodiode;

a controlling section that controls an opening and closing operation of the readout switch of each of the M×N pixel units $P_{1,1}$ to $P_{M,N}$ in the photodetecting section;

a readout wiring $L_O$,n connected with a readout switch of each of the M pixel units $P_{1,n}$ to $P_{M,n}$ of an n-th column in the photodetecting section, where n is an integer not less than 1 and not more than N; and a signal readout section connected with each of the readout wirings $L_{O,1}$ to $L_{O,N}$, for reading signals from the readout wiring $L_{O,1}$ to $L_{O,N}$, wherein the controlling section, when in a first imaging mode, makes a voltage value according to an amount of charges generated in the photodiode of each of the M×N pixel units to $P_{1,1}$ to $P_{M,N}$ in the photodetecting section be output from the signal readout section, and the controlling section, when in a second imaging mode, makes a voltage value according to an amount of charges generated in the photodiode of each pixel unit $P_{m,n}$ included in a specific range of consecutive $M_1$ rows in the photodetecting section be output from the signal readout section, and wherein the solid-state image pickup apparatus comprises, between the specific range in the photodetecting section and another range excluding the specific range, a disconnecting switch provided on each readout wiring $L_{O,n}$, and wherein the controlling section closes the disconnecting switch when in the first imaging mode, and opens the disconnecting switch when in the second imaging mode, wherein $M_1$ is an integer less than M, and wherein m is an integer not less than 1 and not more than M.

7. A solid-state image pickup apparatus according to claim 6, including discharging means that discharges a junction capacitance section of the photodiode in each pixel unit $P_{m,n}$ of another range excluding the specific range in the photodetecting section when in the second imaging mode.

8. A solid-state image pickup apparatus according to claim 6, wherein the controlling section differentiates a gain being a ratio of an output voltage value to an input charge amount in the signal readout section between the first imaging mode and second imaging mode.

9. A solid-state image pickup apparatus according to claim 6, further comprising a scintillator section that is provided so as to cover the M×N pixel units $P_{1,1}$ to $P_{M,N}$ in the photodetecting section.

10. An X-ray inspection system including the solid-state image pickup apparatus according to claim 9 and an X-ray generator, which images X-rays output from the X-ray generator and transmitted through an inspection object by the solid-state image pickup apparatus to inspect the inspection object.

* * * * *

UNITED STATES PATENT AND TRADEMARK OFFICE
CERTIFICATE OF CORRECTION

PATENT NO.       : 8,477,907 B2
APPLICATION NO. : 12/989132
DATED            : July 2, 2013
INVENTOR(S)      : Kyushima et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 118 days.

Signed and Sealed this
Eighth Day of September, 2015

Michelle K. Lee
*Director of the United States Patent and Trademark Office*